United States Patent
Masuda

(10) Patent No.: US 9,738,666 B2
(45) Date of Patent: *Aug. 22, 2017

(54) ELECTROLYTE SALT AND ELECTROLYTE FOR ELECTRICITY STORAGE DEVICE, AND ELECTRICITY STORAGE DEVICE

(71) Applicant: NISSHINBO HOLDINGS INC., Tokyo (JP)

(72) Inventor: Gen Masuda, Chiba (JP)

(73) Assignee: NISSHINBO HOLDINGS, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/435,834

(22) PCT Filed: Oct. 7, 2013

(86) PCT No.: PCT/JP2013/077216
§ 371 (c)(1),
(2) Date: Apr. 15, 2015

(87) PCT Pub. No.: WO2014/061484
PCT Pub. Date: Apr. 24, 2014

(65) Prior Publication Data
US 2015/0291633 A1    Oct. 15, 2015

(30) Foreign Application Priority Data
Oct. 16, 2012  (JP) .................. 2012-229110

(51) Int. Cl.
| | | |
|---|---|---|
| H01G 11/62 | (2013.01) |
| H01M 10/052 | (2010.01) |
| C07F 7/08 | (2006.01) |
| C07C 211/63 | (2006.01) |
| C07C 217/08 | (2006.01) |
| C07D 207/06 | (2006.01) |
| C07D 487/10 | (2006.01) |
| H01G 9/035 | (2006.01) |
| H01G 11/04 | (2013.01) |
| H01M 10/0568 | (2010.01) |
| H01G 9/145 | (2006.01) |

(52) U.S. Cl.
CPC .......... *C07F 7/0818* (2013.01); *C07C 211/63* (2013.01); *C07C 217/08* (2013.01); *C07D 207/06* (2013.01); *C07D 487/10* (2013.01); *H01G 9/035* (2013.01); *H01G 11/04* (2013.01); *H01G 11/62* (2013.01); *H01G 9/145* (2013.01); *H01M 10/052* (2013.01); *H01M 10/0568* (2013.01); *Y02E 60/13* (2013.01)

(58) Field of Classification Search
CPC .......... H01G 2009/0007; H01G 9/035; H01G 9/145; H01G 9/038; H01G 11/62; H01G 11/04; C07F 7/0818; C07F 207/06; C07F 487/10; C07F 217/08; C07F 211/63
See application file for complete search history.

(56) References Cited

U.S. PATENT DOCUMENTS

| | | | | |
|---|---|---|---|---|
| 3,141,898 | A | * | 7/1964 | Van Dyke ............. C07F 7/0818 356/243.1 |
| 4,725,926 | A | | 2/1988 | Morimoto et al. |
| 6,900,257 | B2 | * | 5/2005 | Chowdhury .......... C07C 211/63 524/131 |
| 7,297,289 | B2 | | 11/2007 | Sato et al. |
| 7,471,502 | B2 | | 12/2008 | Sato et al. |
| 9,221,847 | B2 | * | 12/2015 | Masuda ............... C07D 295/08 |
| 2004/0030015 | A1 | | 2/2004 | Chowdhury et al. |

FOREIGN PATENT DOCUMENTS

| | | |
|---|---|---|
| JP | 61-32509 A | 2/1986 |
| JP | 62-252927 A | 11/1987 |
| JP | 63-173312 A | 7/1988 |
| JP | 10-55717 A | 2/1998 |
| JP | 2007-161733 A | 6/2007 |
| JP | 2010-282836 A | 12/2010 |
| WO | 2009/020038 A1 | 2/2009 |
| WO | 2013/005712 A1 | 1/2013 |

OTHER PUBLICATIONS

The Derwent abstract for WO 2009-20038, Feb. 12, 2009*
International Search Report dated Dec. 3, 2013 issued in corresponding application No. PCT/JP2013/077216.

* cited by examiner

*Primary Examiner* — Carol M Koslow
(74) *Attorney, Agent, or Firm* — Westerman, Hattori, Daniels & Adrian, LLP

(57) ABSTRACT

Provided is an electrolyte salt comprising a quaternary ammonium cation indicated by formula (1) and a trimethylsilyl alkanesulfonate anion indicated by formula (2).

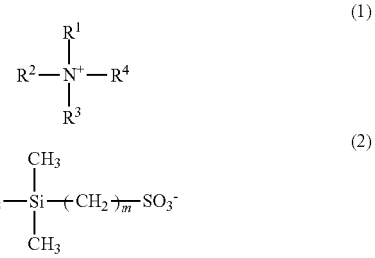

Figure 1:
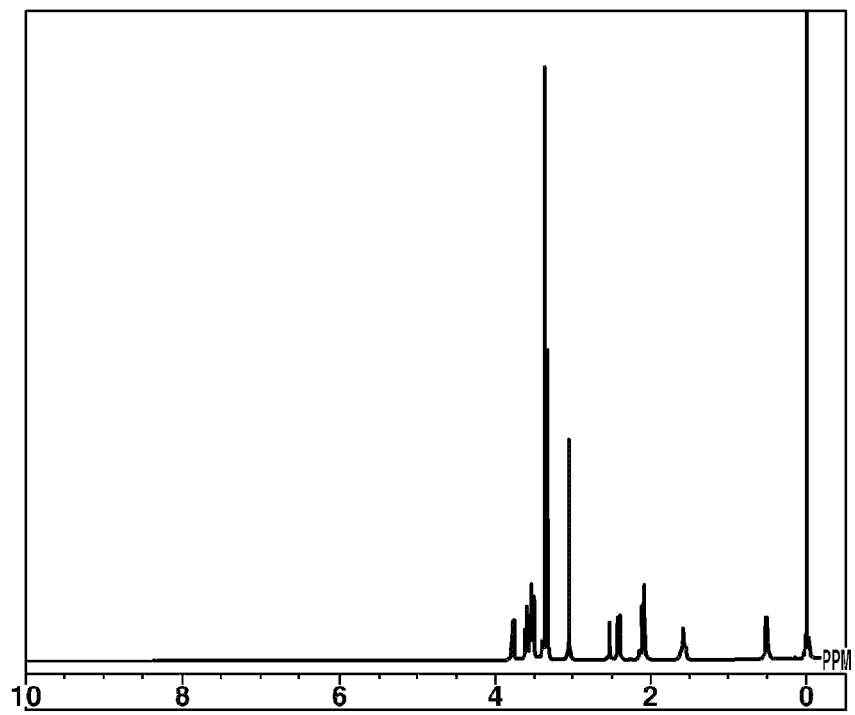

(In the formula, $R^1$-$R^4$ each independently indicate a C1-4 alkyl group or an alkoxyalkyl group indicated by —$(CH_2)_n$—OR. Any two among $R^1$-$R^4$ can mutually bond and form a ring together with a nitrogen atom to which same have bonded. The remaining two can mutually bond and form a spiro ring having a nitrogen atom as the spiro atom therefor. R indicates a methyl group or an ethyl group. n indicates 1 or 2 and m indicates 2 or 3.)

13 Claims, 5 Drawing Sheets

ELECTROLYTE SALT AND ELECTROLYTE FOR ELECTRICITY STORAGE DEVICE, AND ELECTRICITY STORAGE DEVICE

TECHNICAL FIELD

The present invention relates to an electrolyte salt for electrical storage devices, an electrolyte containing the same, and an electrical storage device containing such an electrolyte.

BACKGROUND ART

Nonaqueous electrolyte-type electrical double-layer capacitors have the characteristic of being chargeable and dischargeable at a large current, and thus are promising as energy storage devices for electric cars, auxiliary power supplies and the like.

Nonaqueous electrolyte-type electrical double-layer capacitors are composed of, for example, a positive/negative pair of polarizable electrodes and a nonaqueous electrolyte. The nonaqueous electrolyte is generally composed of an electrolyte salt and a nonaqueous organic solvent. Many studies have hitherto been conducted on combinations of these electrolyte salts and nonaqueous organic solvents. Quaternary ammonium salts (see, for example, Patent Documents 1 to 3), quaternary phosphonium salts (see, for example, Patent Document 4) and the like are widely used as electrolyte salts because of their solubility and degree of dissociation in organic solvents and because of their broad range of electrochemical stability.

However, because these electrolyte salts contain halogen atoms such as fluorine atoms on the anions, they pose problems in terms of the environmental impact. Improvements are desired in this respect.

Electrolyte salts used in electrochemical applications such as electrolytes for nonaqueous electrolyte-type electrical double-layer capacitors are required to have electrochemical properties such as a high ionic conductivity and a wide potential window. However, electrolyte salts which are halogen-free and have a wide potential window have not hitherto been known.

CITATION LIST

Patent Documents

Patent Document 1: JP-A S61-32509
Patent Document 2: JP-A S63-173312
Patent Document 3: JP-A H10-55717
Patent Document 4: JP-A S62-252927

SUMMARY OF INVENTION

Technical Problem

It is therefore an object of the present invention to provide electrolyte salts which do not contain halogen atoms and have a wide potential window compared with conventional electrolyte salts, electrolytes containing such electrolyte salts, and electrical storage devices containing such electrolytes.

Solution to Problem

The inventor, as a result of extensive investigations aimed at achieving the above objects, has discovered that a salt which is composed of a specific quaternary ammonium cation and a trimethylsilyl alkanesulfonate anion has a wide potential window compared with conventional electrolyte salts.

Accordingly, the invention provides the following electrolyte salt and electrolyte for electrical storage devices, and the following electrical storage device.

1. An electrolyte salt for electrical storage devices, the electrolyte salt including a quaternary ammonium cation of formula (1) below and a trimethylsilyl alkanesulfonate anion of formula (2) below

[Chemical Formula 1]

(1)

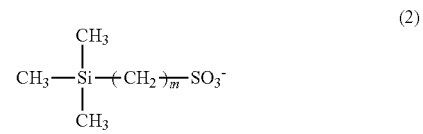

(2)

wherein $R^1$ to $R^4$ are each independently an alkyl group of 1 to 4 carbons or an alkoxyalkyl group of the formula $-(CH_2)_n-OR$, with the proviso that any two of $R^1$ to $R^4$ may be bonded to each other and form a ring together with the nitrogen atom to which they are bonded and the remaining two may be bonded to each other and form a spiro ring with the nitrogen group serving as the spiro atom; R is a methyl group or an ethyl group; n is 1 or 2; and m is 2 or 3.

2. The electrolyte salt for electrical storage devices of 1 above, wherein at least one of $R^1$ to $R^4$ is an alkoxyalkyl group of the formula $-(CH_2)_n-OR$.

3. The electrolyte salt for electrical storage devices of 1 or 2 above, wherein n is 2.

4. The electrolyte salt for electrical storage devices of 1 above, wherein any two of $R^1$ to $R^4$ are bonded to each other and form a ring together with the nitrogen atom to which they are bonded and the remaining two are bonded to each other and form a spiro ring with the nitrogen group serving as the spiro atom.

5. The electrolyte salt for electrical storage devices of 4 above, wherein the ring is a pyrrolidine ring or the spiro ring is a 1,1'-spirobipyrrolidine ring.

6. The electrolyte salt for electrical storage devices of 1 above, wherein the quaternary ammonium cation is any of the cations of formulas (3) to (6) below

[Chemical Formula 2]

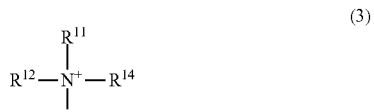

(3)

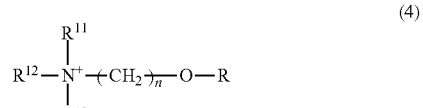

(4)

(5)

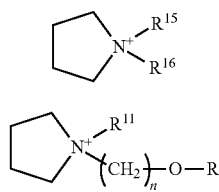

(6)

wherein $R^{11}$ to $R^{14}$ are each independently alkyl groups of 1 to 4 carbons; $R^{15}$ and $R^{16}$ are each independently alkyl groups of 1 to 4 carbons, with the proviso that $R^{15}$ and $R^{16}$ may be bonded to each other and may form a ring together with the nitrogen atom to which they are bonded; and R and n are as defined above.

7. The electrolyte salt for electrical storage devices of 6 above, wherein the quaternary ammonium cation is a cation of formula (4), (5) or (6).
8. An electrolyte containing the electrolyte salt for electrical storage devices of any one of 1 to 7 above.
9. An electrical storage device containing the electrolyte of 8 above.
10. The electrical storage device of 9 above which is an electrical double-layer capacitor.
11. The electrical storage device of 9 above which is an electrolytic capacitor.

Advantageous Effects of Invention

The electrolyte salt for electrical storage devices of the invention is halogen free and thus has little environmental impact. Moreover, it has a wide potential window compared with conventional electrolyte salts and is thus electrochemically stable.

BRIEF DESCRIPTION OF THE DIAGRAMS

Figure 2:
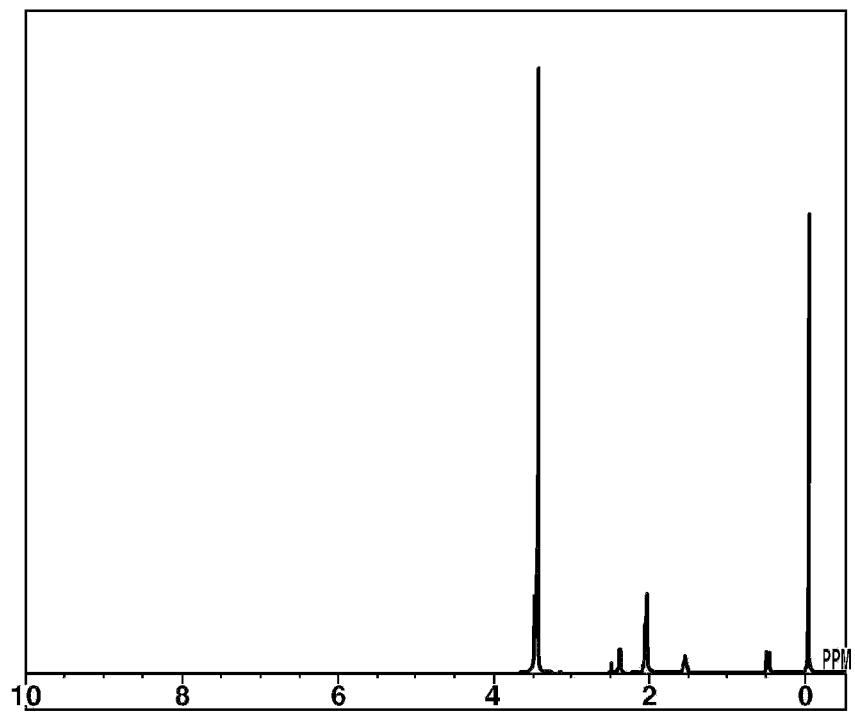
Figure 3:
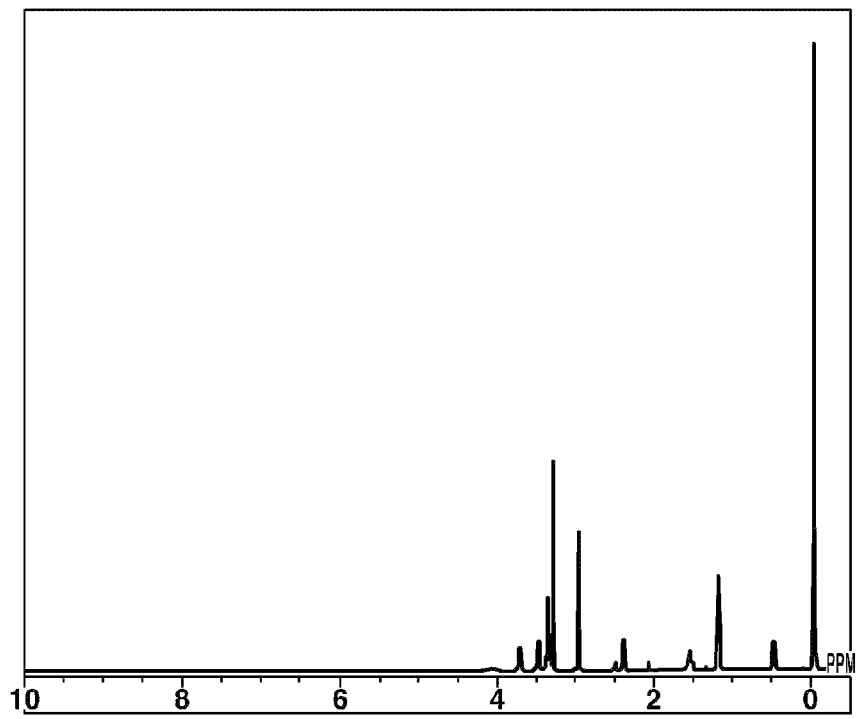
Figure 4:
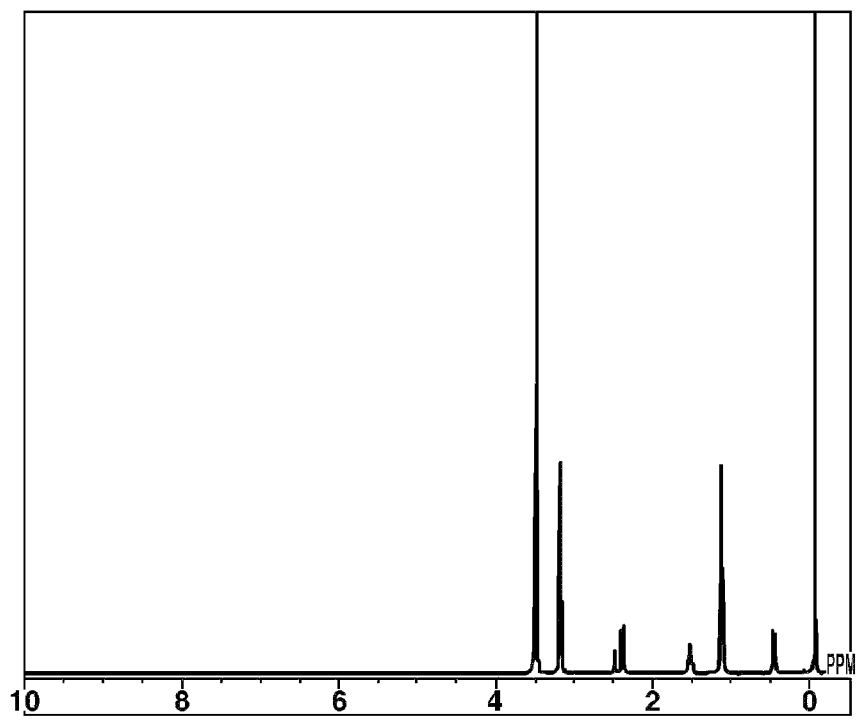
Figure 5:
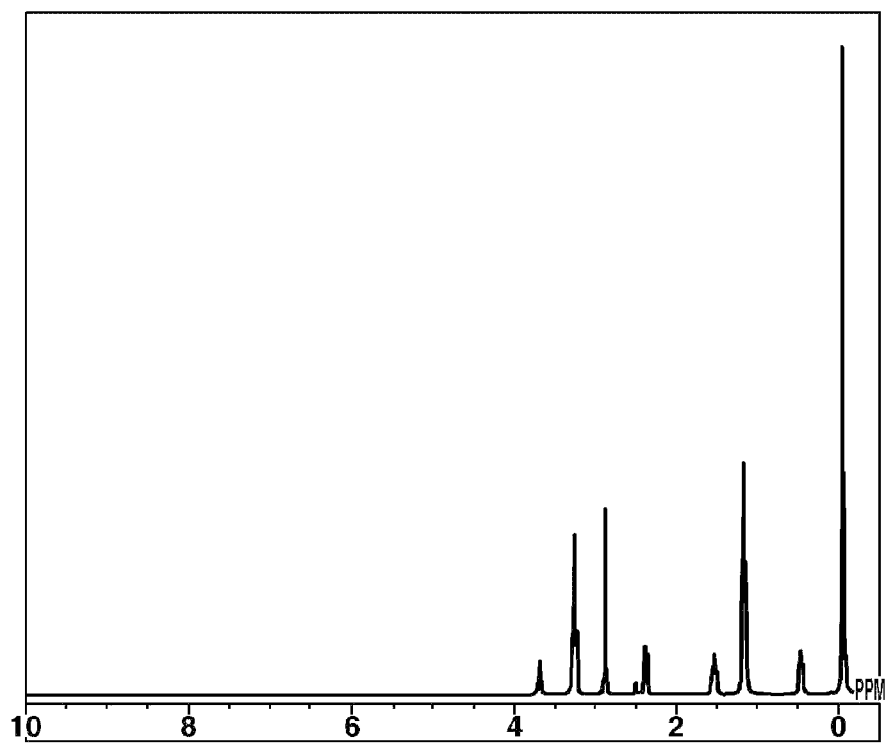
Figure 6:
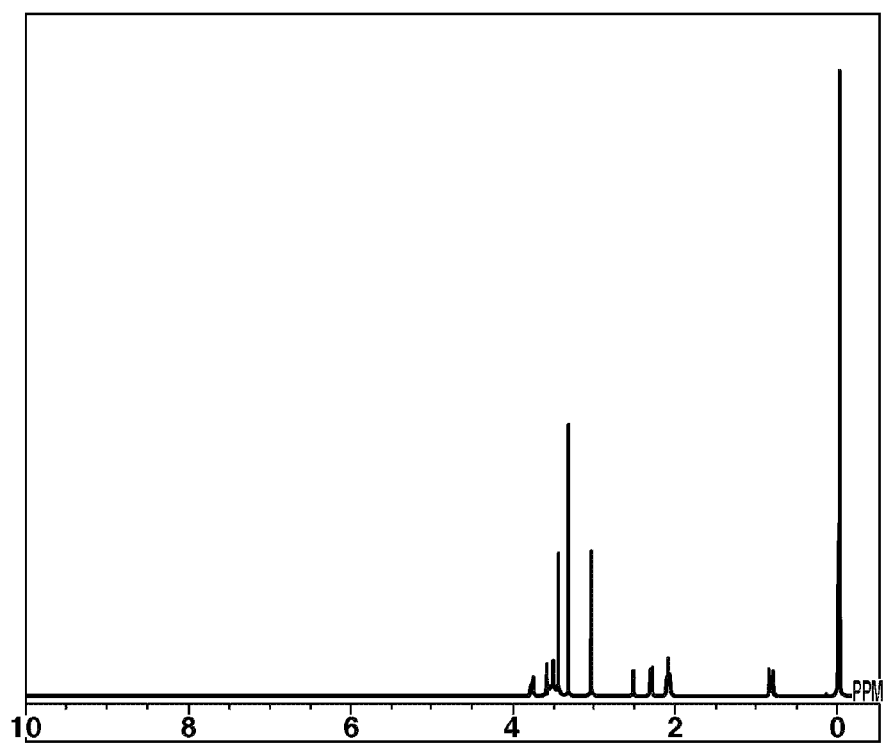
Figure 7:
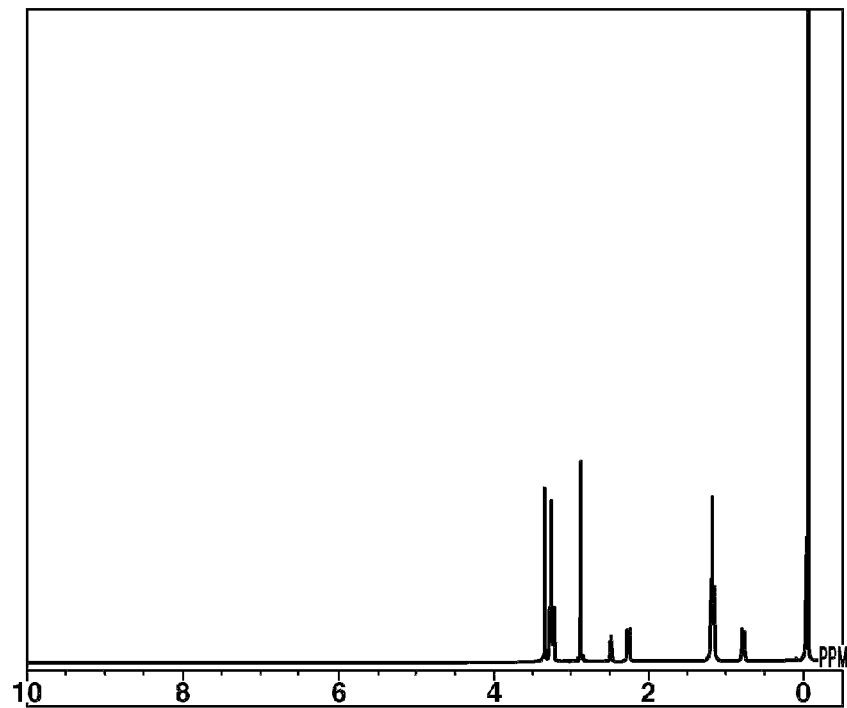
Figure 8:
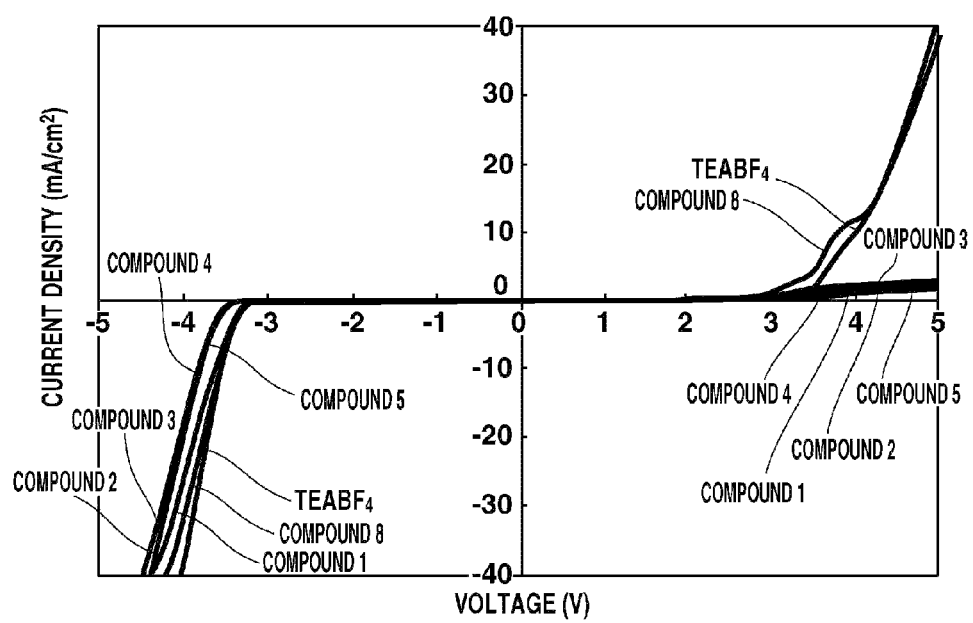
Figure 9:
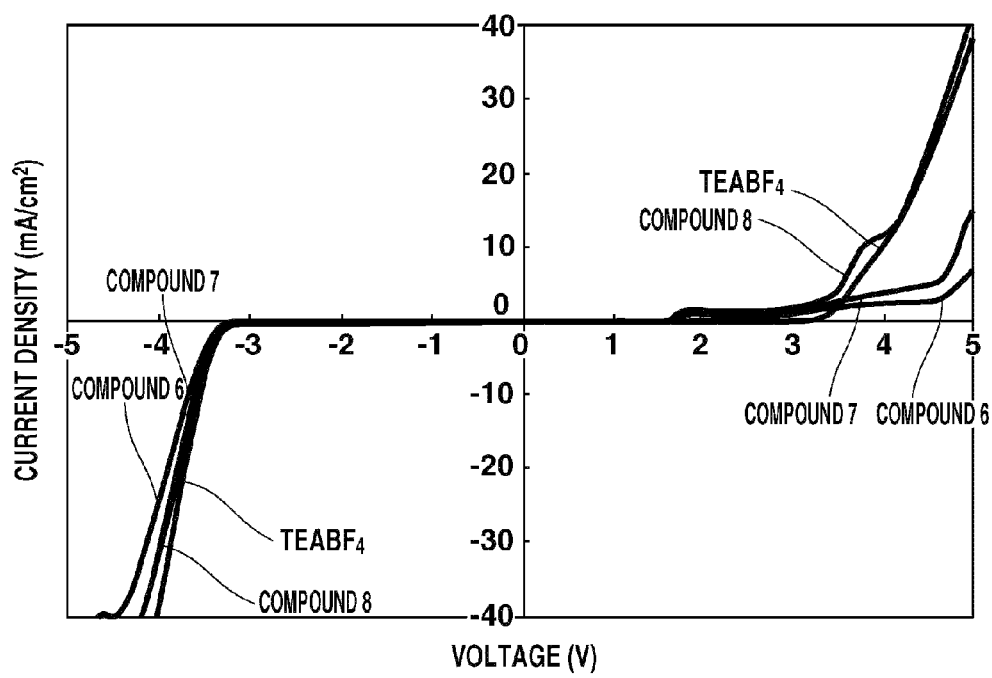

FIG. 1 is an $^1$H-NMR spectrum of Compound 1 obtained in Example 1.
FIG. 2 is an $^1$H-NMR spectrum of Compound 2 obtained in Example 2.
FIG. 3 is an $^1$H-NMR spectrum of Compound 3 obtained in Example 3.
FIG. 4 is an $^1$H-NMR spectrum of Compound 4 obtained in Example 4.
FIG. 5 is an $^1$H-NMR spectrum of Compound 5 obtained in Example 5.
FIG. 6 is an $^1$H-NMR spectrum of Compound 6 obtained in Example 6.
FIG. 7 is an $^1$H-NMR spectrum of Compound 7 obtained in Example 7.
FIG. 8 is a chart showing the potential windows of above Compounds 1 to 5 obtained in Examples 1 to 5.
FIG. 9 is a chart showing the potential windows of above Compounds 6 and 7 obtained in Examples 6 and 7.

DESCRIPTION OF EMBODIMENTS

[Electrolyte Salt for Electrical Storage Devices]
The inventive electrolyte salt for electrical storage devices is composed of a quaternary ammonium cation of formula (1) below and a trimethylsilyl alkanesulfonate anion of formula (2) below.

[Chemical Formula 3]

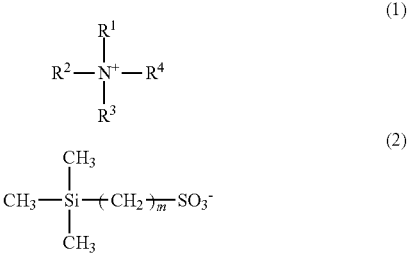

In formula (1), $R^1$ to $R^4$ are each independently an alkyl group of 1 to 4 carbons or an alkoxyalkyl group of the formula —$(CH_2)_n$—OR, with R being a methyl group or an ethyl group and the letter "n" being 1 or 2. The letter "n" is preferred 2.

The alkyl group may be linear, branched or cyclic, and is exemplified by methyl, ethyl, n-propyl, i-propyl, c-propyl, n-butyl, s-butyl, i-butyl and t-butyl groups. Of these, an alkyl group of 1 to 3 carbons is preferred, a linear alkyl group of 1 to 3 carbons is more preferred, and a methyl group or an ethyl group is even more preferred.

Illustrative examples of alkoxyalkyl groups include methoxymethyl, ethoxymethyl, methoxyethyl and ethoxyethyl. Of these, methoxyethyl and ethoxyethyl are preferred.

Any two of $R^1$ to $R^4$ may be bonded to each other and form a ring together with the nitrogen atom to which they are bonded, and the remaining two may be bonded to each other and form a spiro ring with the nitrogen group serving as the spiro atom. In this case, the any two groups from among $R^1$ to $R^4$ which bond together are preferably each independently linear or branched alkylene groups, and more preferably linear alkylene groups. The number of carbons on the alkylene group is preferably from 2 to 8, and more preferably from 4 to 6. In this case, the ring is exemplified by an aziridine ring, azetidine ring, pyrrolidine ring, piperidine ring and azepane ring, with a pyrrolidine ring or a piperidine ring being preferred, and a pyrrolidine ring being more preferred. The spiro ring is most preferably a 1,1'-spirobipyrrolidine ring.

The cation of formula (1) is preferably one of formulas (3) to (6) below.

[Chemical Formula 4]

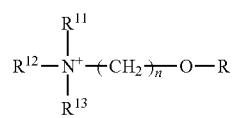

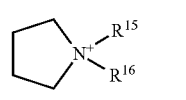

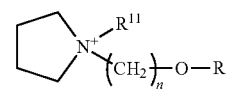

In these formulas, $R^{11}$ to $R^{14}$ are each independently alkyl groups of 1 to 4 carbons. $R^{15}$ and $R^{16}$ are each independently alkyl groups of 1 to 4 carbons, with the proviso that $R^{15}$ and $R^{16}$ may be bonded to each other and may form a ring together with the nitrogen atom to which they are bonded. R and n are as defined above. These alkyl groups are exemplified by the same groups as mentioned above. In cases where $R^{15}$ and $R^{16}$ are bonded to each other, $-R^{15}\text{-}R^{16}-$ is exemplified by the same groups as mentioned above as groups formed by any two of $R^1$ to $R^4$ bonding with each other.

Of the above cations, those of formula (4), (5) or (6) in particular are preferred from the standpoint of excellent solubility of the electrolyte.

In formula (2), "m" is 2 or 3. From the standpoint of achieving a particularly high voltage resistance, 3 is preferred.

Illustrative examples of electrolyte salts of the invention include, but are not limited to, the following.

[Chemical Formula 5]

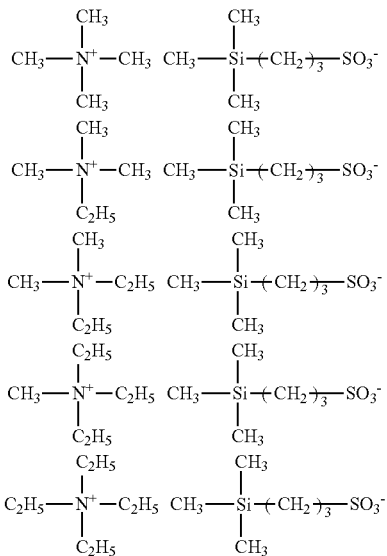

[Chemical Formula 6]

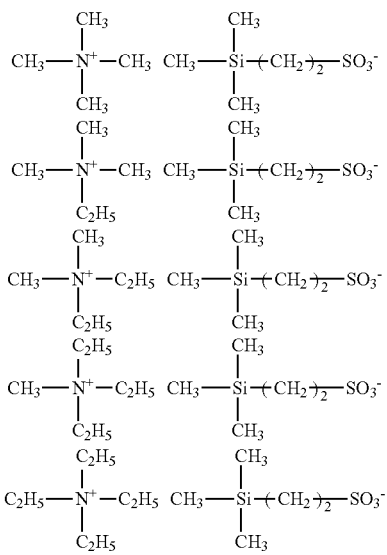

[Chemical Formula 7]

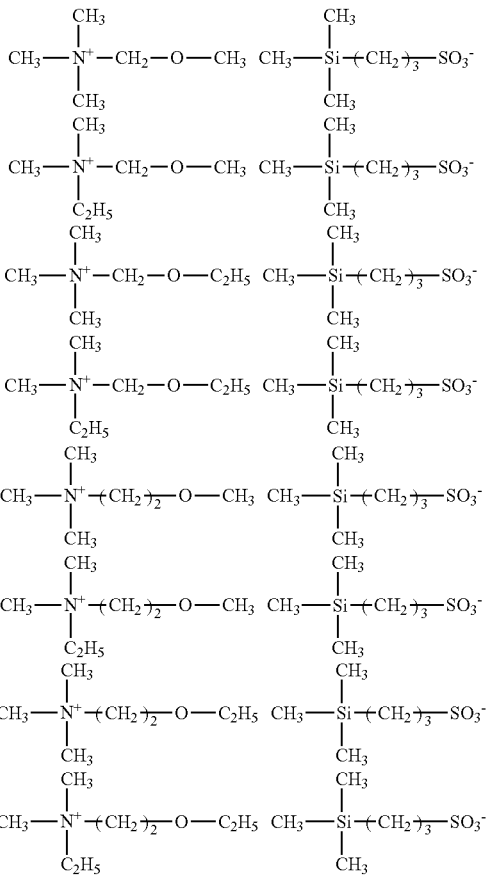

[Chemical Formula 8]

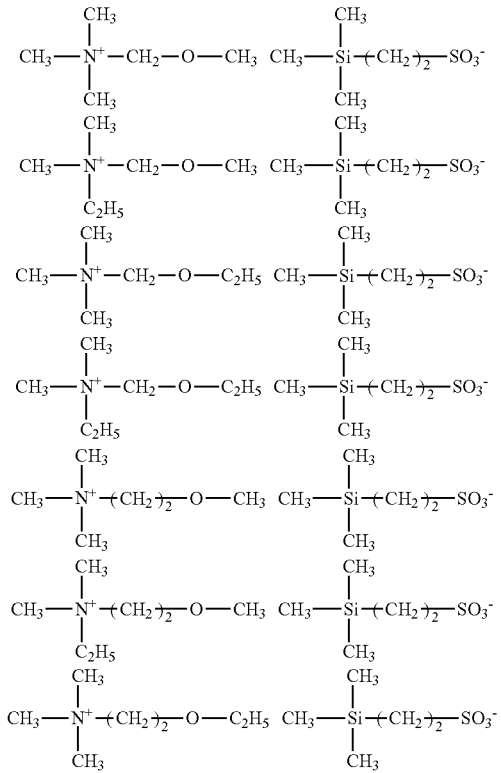

-continued

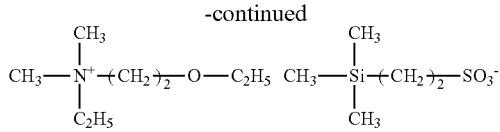

[Chemical Formula 9]

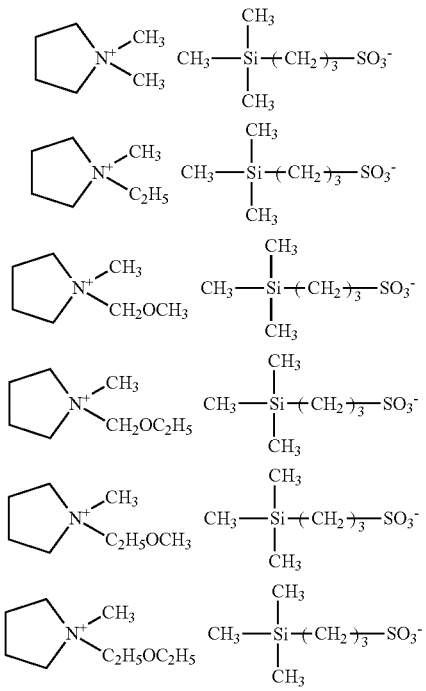

[Chemical Formula 10]

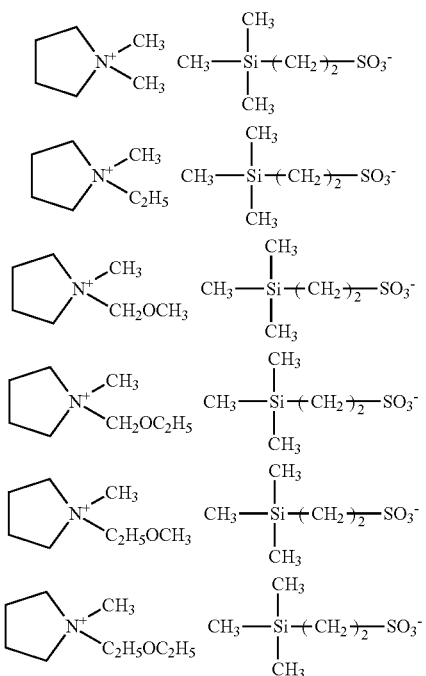

[Chemical Formula 11]

-continued

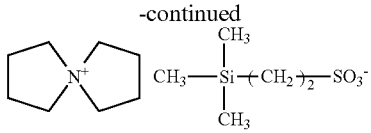

[Method of Producing Electrolyte Salt for Electrical Storage Devices]

The inventive electrolyte salt for electrical storage devices can be produced by using an ion-exchange resin to carry out ion exchange on, for example, the quaternary ammonium salt of formula (7) below and the trimethylsilyl alkanesulfonate salt of formula (8) below.

[Chemical Formula 12]

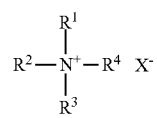  (7)

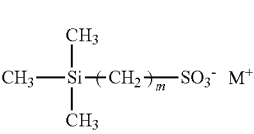  (8)

In these formulas, $R^1$ to $R^4$ and m are as defined above, X is a halogen atom, and $M^+$ is a monovalent metal ion.

Specifically, first, an aqueous solution of the quaternary ammonium salt in formula (7) is passed through a column packed with a cation-exchange resin, thereby causing the cations of the quaternary ammonium salt to be supported on the cation-exchange resin, and the column is rinsed by passing water through. Next, the trimethylsilyl alkanesulfonate salt of formula (8) is passed through the column and the eluate is recovered and purified, thereby giving the target electrolyte salt.

The cation-exchange resin used here may be a commonly used cation-exchange resin, although the use of a strongly acidic cation-exchange resin is preferred. Such a cation-exchange resin may be acquired as a commercial product.

The quaternary ammonium salt of formula (7) may be synthesized by a known method. For example:

(A) In cases where the cation of the quaternary ammonium salt is a cation of formula (3), the salt can be synthesized by reacting a tertiary amine with an alkyl halide. It is also possible to use a commercial product as such a quaternary ammonium salt.

(B) In cases where the cation of the quaternary ammonium salt is a cation of formula (4), the salt can be synthesized by first reacting a dialkylamine with an alkoxyalkyl halide to form a tertiary amine, then reacting the tertiary amine with an alkyl halide.

(C) In cases where the cation of the quaternary ammonium salt is a cation of formula (5), the salt can be synthesized by first reacting pyrrolidine with an alkyl halide to form a tertiary amine, then reacting the tertiary amine with an alkyl halide. In cases where, in the cation of formula (5), $R^{15}$ and $R^{16}$ are bonded to each other and form a ring together with the nitrogen atom to which they are bonded, the salt can be synthesized by reacting pyrrolidine with an alkane dihalide.

(D) In cases where the cation of the quaternary ammonium salt is a cation of formula (6), the salt can be synthesized by first reacting a cyclic secondary amine such as pyrrolidine or piperidine with an alkoxyalkyl halide to form a tertiary amine, then reacting the tertiary amine with an alkyl halide.

The sulfonate salt of formula (8) can be synthesized using a hitherto known method. Alternatively, the sulfonate salt may be acquired as a commercial product.

Examples of the halogen atom represented above as X include fluorine, chlorine, bromine and iodine atoms. Of these, chlorine, bromine and iodine atoms are preferred.

Examples of the metal ion represented above as $M^+$ include sodium, potassium and silver ions.

Alternatively, the electrolyte salt of the invention can be prepared by reacting the quaternary ammonium salt of formula (7) with the sulfonate salt of formula (8) in a solvent. In this case, the solvent may be either water or an organic solvent.

The relative proportions in which the quaternary ammonium salt and the sulfonate salt are used in the above reaction may be set to a molar ratio of from about 5:1 to about 1:5. Carrying the reaction out at a ratio close to 1:1 is generally preferred.

Following reaction completion, the target substance can be obtained by carrying out an ordinary work-up.

Another exemplary method of preparing the electrolyte salt of the invention is a neutralization method that uses an ion-exchange resin. In this neutralization method, first a sulfonate salt and an onium salt are converted into a sulfonic acid and a quaternary ammonium hydroxide using, respectively, a cation-exchange resin and an anion-exchange resin, following which the two are mixed together to give the electrolyte salt.

In cases where this neutralization method is employed in the invention, there is no particular limitation on the counterions so long as both the sulfonate salt and the onium salt undergo ion exchange. However, from the standpoint of cost, the sulfonate salt is preferably, for example, a sodium salt or a potassium salt. The counterion for the onium salt is preferably a halide ion. From the standpoint of cost, a chloride ion or a bromide ion is especially preferred.

The molar ratio between the sulfonic acid and the quaternary ammonium hydroxide in the above neutralization reaction is not particularly limited, and may be set to from about 5:1 to about 1:5. From the standpoint of cost, the reaction is preferably carried out at a ratio close to 1:1, with the neutralization point of the aqueous phase most preferably serving as the reaction endpoint.

[Electrolyte]

The electrolyte salt of the invention is particularly useful in electrolytes for use in electrical storage devices. Electrolytes containing the electrolyte salt of the invention have a wider potential window than conventional electrolytes, and are thus electrochemically stable.

The electrolyte of the invention may be employed in any of the following forms:

[1] an electrolyte composed solely of the electrolyte salt of the invention;
[2] an electrolyte obtained by adding another electrolyte salt to the electrolyte of [1];
[3] an electrolyte containing the electrolyte salt of the invention and an organic solvent; and
[4] an electrolyte obtained by adding another electrolyte salt to the electrolyte of [3].

Above electrolytes [1] and [2] may be used only in cases where the electrolyte salt of the invention is a so-called ionic liquid. Electrolytes [3] and [4] may be used in cases where the electrolyte salt of the invention is either an ionic liquid or a solid.

The organic solvent used in above form [3] or [4] is not particularly limited, and may be suitably selected from among organic solvents commonly used in electrolytes for electrical storage devices.

For example, in cases where the electrical storage device is an electrical double-layer capacitor, preferred organic solvents include acyclic ether solvents such as dibutyl ether, 1,2-dimethoxyethane, 1,2-ethoxymethoxyethane, methyl diglyme, methyl triglyme, methyl tetraglyme, ethyl monoglyme, ethyl diglyme, butyl diglyme, ethyl cellosolve, ethyl carbitol, butyl cellosolve and butyl carbitol; cyclic ether solvents such as tetrahydrofuran, 2-methyltetrahydrofuran, 1,3-dioxolane and 4,4-dimethyl-1,3-dioxane; cyclic ester solvents such as γ-butyrolactone, γ-valerolactone, δ-valerolactone, 3-methyl-1,3-oxazolidin-2-one and 3-ethyl-1,3-oxazolidin-2-one; amide solvents such as N-methylformamide, N,N-dimethylformamide, N-methylacetamide and N-methylpyrrolidinone; carbonate solvents such as diethyl carbonate, dimethyl carbonate, ethyl methyl carbonate, propylene carbonate, ethylene carbonate and styrene carbonate; imidazolidinone solvents such as 1,3-dimethyl-2-imidazolidinone; sulfolane solvents such as sulfolane, methyl sulfolane and 2,4-dimethyl sulfolane; and these various types of organic solvents in which a hydrogen atom or an alkyl group has been substituted with a fluoroalkyl group, examples of which include fluorinated solvents such as fluorinated propylene carbonate and fluorinated γ-butyrolactone. These may be used singly or may be used in mixtures of two or more.

In cases where the electrical storage device is an electrolytic capacitor, preferred organic solvents include monohydric alcohols such as methanol, ethanol, propanol, butanol, pentanol, hexanol, cyclobutanol, cyclopentanol, cyclohexanol and benzyl alcohol; polyhydric alcohols and oxyalcohols such as ethylene glycol, propylene glycol, glycerol, methyl cellosolve, ethyl cellosolve, methoxypropylene glycol and dimethoxypropanol; cyclic ester solvents such as γ-butyrolactone; amide solvents such as N-methylformamide, N,N-dimethylformamide, N-ethylformamide, N,N-diethylformamide, N-methylacetamide, N,N-dimethylacetamide, N-ethylacetamide, N,N-diethylacetamide and hexamethylphosphoric triamide; sulfolane solvents such as sulfolane, 3-methylsulfolane and 2,4-dimethylsulfolane; acylic sulfone solvents such as dimethylsulfone and ethylmethylsulfone; cyclic amide solvents such as N-methyl-2-pyrrolidone; carbonate solvents such as ethylene carbonate, propylene carbonate and isobutylene carbonate; nitrile solvents such as acetonitrile; sulfoxides such as dimethylsulfoxide; and 2-imidazolidinone solvents such as 1,3-dialkyl-2-imidazolidinones (e.g., 1,3-dimethyl-2-imidazolidinone, 1,3-diethyl-2-imidazolidinone and 1,3-di(n-propyl)-2-imidazolidinone) and 1,3,4-trialkyl-2-imidazolidinones (e.g., 1,3,4-trimethyl-2-imidazolidinone).

Of these, the organic solvent used in the inventive electrolyte, in the case of electrical double-layer capacitors, from the standpoint of having a large dielectric constant, a broad electrochemical stability range and a broad service temperature range, and having also an excellent safety, is preferably an organic solvent containing a carbonate solvent, an organic solvent containing a fluorinated solvent, or an organic solvent containing a sulfolane solvent. Specifically, solvents containing propylene carbonate, diethyl carbonate, sulfolane, 2-methylsulfolane or 3-methylsulfolane are preferred. In the case of an electrolytic capacitor, a solvent containing ethylene glycol or sulfolane is preferred.

When the electrolyte is of form [3] or [4] above, the content of the electrolyte salt of the invention in an electrical double layer capacitor is preferably from 0.05 to 2.5 mol/L, and more preferably from 0.5 to 1.5 mol/L. At less than 0.05 mol/L, the desired electrostatic capacitance may be not achievable, whereas at more than 2.5 mol/L, the electrolyte salt of the invention may deposit out at low temperatures. Also, in an electrostatic capacitor, the content of the inventive electrolyte salt within the electrolyte is preferably from 1.0 to 60 wt %, more preferably from 5.0 to 50 wt %, and most preferably from 10 to 40 wt %. At less than 1.0 wt %, a sufficient sparking voltage may not be obtained, whereas at more than 60 wt %, the resistivity may rise.

Other electrolyte salts used in ordinary electrical storage devices may also be added to the electrolyte of the invention. Illustrative examples of such electrolyte salts include, in the case of electrical double-layer capacitors, $(C_2H_5)_4PBF_4$, $(C_3H_7)_4PBF_4$, $(C_4H_9)_4PBF_4$, $(C_6H_{13})_4PBF_4$, $(C_4H_9)_3CH_3PBF_4$, $(C_2H_5)_3(Ph\text{-}CH_2)PBF_4$ (where "Ph" represents a phenyl group), $(C_2H_5)_4PPF_6$, $(C_2H_5)PCF_3SO_2$, $(C_2H_5)_4NBF_4$, $(C_4H_9)_4NBF_4$, $(C_6H_{13})_4NBF_4$, $(C_2H_5)_6NPF_6$, $LiBF_4$ and $LiCF_3SO_3$.

The content of other electrolyte salts is not particularly limited, provided the objects of the invention are attainable, although it is generally preferable to set such a content so as to be from about 0.1 mole to about 100 moles per mole of the electrolyte of the invention.

In the case of electrolytic capacitors, any of the following which are used in electrolytes for conventional aluminum electrolytic capacitors may also be added: ammonium salts, amine salts, quaternary ammonium salts and the quaternary salts of cyclic amidine compounds in which the conjugate base of an acid serves as the anion component.

The amine making up the above amine salt is exemplified by primary amines such as methylamine, ethylamine, propylamine, butylamine and ethylenediamine; secondary amines such as dimethylamine, diethylamine, dipropylamine, methylethylamine and diphenylamine; and tertiary amines such as trimethylamine, triethylamine, tripropylamine, triphenylamine and 1,8-diazabicyclo[5,4,0]-undecene-7.

The quaternary ammonium cation making up the above quaternary ammonium salt is exemplified by tetraalkylammonium cations such as tetramethylammonium, tetraethylammonium, tetrapropylammonium, tetrabutylammonium, methyltriethylammonium and dimethyldiethylammonium cations; and pyridinium cations such as 1-methylpyridinium, 1-ethylpyridinium and 1,3-diethylpyridinium cations.

The cation making up the quaternary salt of the above cyclic amidine compound is exemplified by cations resulting from the quaternization of the following compounds: imidazole compounds such as 1-methylimidazole, 1,2-dimethylimidazole, 1,4-dimethyl-2-ethylimidazole and 1-phenylimidazole; nitroimidazole compounds such as 1-methyl-4(5)-nitroimidazole; aminoimidazole compounds such as 1,2-dimethyl-5(4)-aminoimidazole; benzoimidazole compounds such as 1-methylbenzoimidazole and 1-methyl-2-benzylbenzo-imidazole; compounds having a 2-imidazoline ring, such as 1-methylimidazoline, 1,2-dimethylimidazoline, 1,2,4-trimethylimidazoline, 1,4-dimethyl-2-ethylimidazoline and 1-methyl-2-phenylimidazoline; and compounds having a tetrahydropyrimidine ring, such as 1-methyl-1,4,5,6-tetra-hydropyrimidine, 1,2-dimethyl-1,4,5,6-tetrahydropyrimidine, 1,8-diazabicyclo[5.4.0]undecene-7,1,5-diazabicyclo[4.3.0]-nonene-5.

The above anion component is exemplified by adipic acid, glutaric acid, succinic acid, benzoic acid, isophthalic acid, phthalic acid, terephthalic acid, maleic acid, toluic acid enanthic acid, malonic acid, formic acid, decanedicarboxylic acids such as 1,6-decandicarboxylic acid and 5,6-decanedicarboxylic acid, octanedicarboxylic acids such as 1,7-octanedicarboxylic acid, organic acids such as azelaic acid and sebacic acid, boric acid, polyhydric alcohol complex compounds of boric acid obtained from boric acid and a polyhydric alcohol, and conjugate bases of inorganic acids such as phosphoric acid, carbonic acid and silicic acid.

[Electrical Storage Devices]

The inventive electrolyte can be advantageously used as an electrolyte for electrical storage devices. Here, "electrical storage device" refers to a device or element which is capable of chemically, physically or physicochemically storing electricity. Examples of such devices include devices which can be electrically charged and discharged, such as secondary batteries (e.g., lithium ion batteries), electrical double-layer capacitors and electrolytic capacitors. The electrolyte of the invention is preferably an electrolyte for an electrical double-layer capacitor or for an electrolytic capacitor.

The basic structure of the electrical storage device may be the same as that in hitherto known electrical storage devices. Generally, a positive electrode and a negative electrode are arranged opposite one another across an intervening separator, and this structure is impregnated with an electrolyte. In the electrical storage device of this invention, the electrolyte of the invention is used as the foregoing electrolyte.

[Electrical Double-Layer Capacitor]

The electrical double layer capacitor of the invention includes a pair of polarizable electrodes, a separator disposed between these polarizable electrodes, and the above-described electrolyte.

The polarizable electrodes are each composed of a current collecting substrate and an electrode filler that has been coated onto the surface of the substrate. These polarizable electrodes are generally produced by mixing together an electrode active material, a conductive material and a binder or the like in a solvent such as N-methylpyrrolidone to form an electrode filler slurry, coating the slurry onto a current collecting substrate, then drying and rolling the applied slurry.

The current collecting substrates and the electrode active material, conductive material and binder which make up the electrode fillers are not particularly limited, and may be suitably selected from among known materials used in electrical double-layer capacitors.

Illustrative examples of electrode active materials include activated carbon obtained by firing and activating various starting materials such as coconut shell, coffee beans, bamboo, sawdust, coal pitch, petroleum pitch, coke, mesophase carbon, a phenolic resin or a vinyl chloride resin.

The conductive material is exemplified by carbon black, ketjen black, acetylene black, carbon whiskers, carbon fibers, natural graphite, synthetic graphite, titanium oxide, ruthenium oxide, and metallic fibers of aluminum, nickel or the like. The amount of conductive material added may be set to, for example, from 0.1 to 20 parts by weight per 100 parts by weight of the electrode active material.

Examples of binders that may be used include polytetrafluoroethylene, polyvinylidene fluoride (PVDF), carboxymethylcellulose, fluoroolefin copolymer-crosslinked polymers, polyvinyl alcohol, polyacrylic acid, polyimide, petroleum pitch, coal pitch and phenolic resin. The amount of binder added may be set to, for example, from 0.5 to 20 parts by weight per 100 parts by weight of the electrode active material.

The current collecting substrate making up the positive electrode is exemplified by aluminum foil and aluminum oxide foil. The current collecting substrate making up the negative electrode is exemplified by copper foil, nickel foil, and metal foils on the surface of which has been formed a copper plating film or a nickel plating film.

The separator used may be suitably selected from among known separators. Illustrative examples include polyolefin nonwoven fabric, PTFE porous film, kraft paper, sheet laid from a blend of rayon fibers and sisal hemp fibers, manila hemp sheet, glass fiber sheet, cellulose-based electrolytic paper, paper made from rayon fibers, and paper made from a blend of cellulose and glass fibers. Alternatively, these may be combined and used as a separator composed of a plurality of layers.

The electric double layer capacitor of the invention can be assembled by stacking, fan-folding or winding an electric double layer capacitor assembly composed of a pair of polarizable electrodes and, if necessary, a separator therebetween. The cell assembly is then placed within a capacitor housing such as a can or a laminate pack. The assembly is then filled with the electrolyte, following which the housing is mechanically sealed if it is a can or heat-sealed if it is a laminate pack. The method of manufacture is not limited to this, so long as use is made of a technique that is suitable for the type of members making up the capacitor.

[Electrolytic Capacitor]

The electrolytic capacitor of the invention is most preferably an aluminum electrolytic capacitor. This generally has a structure in which an electrolyte-impregnated separator is sandwiched between, as the positive electrode, an aluminum foil on the surface of which an insulating alumina layer has been formed by anodization and, paired therewith as the negative electrode, an aluminum foil.

In the electrolytic capacitor, the aluminum foils used in the positive electrode and the negative electrode generally have been etched in order to increase the surface area and thereby raise the electrostatic capacitance.

The separator used in the electrolytic capacitor may be similar to the separator described above in connection with the electrical double-layer capacitor.

The electrical storage device of the invention is highly suitable for use as a memory backup power supply for cell phones, notebook computers and handheld devices, as a power supply for cell phones and portable acoustic devices, as an uninterruptible power supply for personal computers and other equipment, and as various types of low-current electrical storage devices such as load leveling power supplies used in combination with solar power generation or wind power generation. Moreover, electrical double layer capacitors which can charged and discharged at a high current are suitable for use as high-current electrical storage devices in applications that require a large current, such as electric cars, electrical power tools, copiers, construction equipment and transportation equipment.

EXAMPLES

Working Examples of the invention and Comparative Examples are given below by way of illustration, although the invention is not limited by the following Examples.

The analytical instruments and conditions used in the Examples were as follows.

[1] $^1$H-NMR Spectrum
  Instrument: AL-400, from JEOL Ltd.
  Solvent: Deuterated DMSO
[2] Cyclic Voltammetry Measurement
  Instrument: HSV-100 Electrochemical Measurement System, from Hokuto Denko Corporation
  Measurement conditions:
    Using a glassy carbon electrode as the working electrode, a platinum electrode as the counterelectrode, and a Ag/Ag$^+$ reference electrode, measurement was carried out at a sweep rate of 10 mV/sec.

Example 1

Synthesis of Compound 1

Compound 1 of the following formula was synthesized.

[Chemical Formula 13]

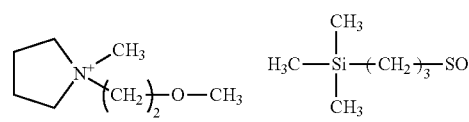

Compound 1

Pyrrolidine (Wako Pure Chemical Industries, Ltd.), 1.51 parts by weight, and 2-methoxyethyl chloride (Kanto Chemical Co., Inc.), 1.00 part by weight, were mixed together and reacted for 1 hour under refluxing. Following the reaction, the reaction mixture was separated into two phases, then left to cool for a while, whereupon the bottom phase solidified. The top phase alone was collected by decantation, and purification was carried out by vacuum distillation. This distillation gave 0.96 part by weight of the target substance N-2-methoxyethylpyrrolidine (boiling point, 76° C.; vapor pressure, 45 mmHg) in a yield of 70%.

Next, 1.00 part by weight of the resulting N-2-methoxyethylpyrrolidine was mixed with a two-fold volume of toluene (Wako Pure Chemical Industries, Ltd.), the mixture was placed in an autoclave, and the interior of the system was flushed with nitrogen. The system was closed, after which about 1.00 part by weight of methyl chloride gas (Nittoku Kagaku Kogyo KK) was added under stirring at room temperature. During introduction of the methyl chloride gas, the temperature and internal pressure both rose; at the highest point, the temperature rose to about 53° C. and the internal pressure rose to 5.5 kgf/cm$^2$. The reaction was effected in this way without heating; after 2 days, about 0.75 part by weight of methyl chloride gas was added. The reaction was additionally continued for one day, after which the pressure was released. The crystals that had formed within the system were separated off by vacuum filtration and then dried using a vacuum pump, thereby giving 1.29 parts by weight of N-2-methoxyethyl-N-methylpyrrolidinium chloride (yield, 92%).

The cation-exchange resin Amberlist 15JS-HG.DRY (Organo Corporation) was packed into an approximately 20 mL column, and exchanged to the hydrogen form. An aqueous solution of 55 g of N-2-methoxyethyl-N-methylpyrrolidinium chloride dissolved in 100 mL of deionized water was passed through the packed column, thereby converting the resin to the N-2-methoxyethyl-N-methylpyrrolidinium form. Following conversion, deionized water was thoroughly passed through the column and the eluate was confirmed to be neutral. An aqueous solution of 7.57 g of sodium 3-(trimethylsilyl)-1-propanesulfonate (from Sigma-Aldrich Co.) dissolved in 150 mL of deionized water was then passed through the column. The eluate was recovered, then concentrated by reducing the pressure using a vacuum pump and removing the water by distillation. A vacuum was then pulled for 1.5 hours while heating the distillation residue to 110° C. on an oil bath, thereby giving 11.3 g of the target substance: Compound 1 (yield, 95%). The ¹H-NMR spectrum of Compound 1 thus obtained is shown in FIG. 1.

Example 2

Synthesis of Compound 2

Compound 2 of the following formula was synthesized.

[Chemical Formula 14]

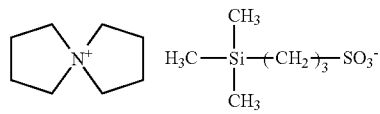

Compound 2

Fifty parts by weight of 1,4-dibromobutane (Tokyo Chemical Industry Co., Ltd.) and 38.4 parts by weight of potassium carbonate (Wako Pure Chemical Industries, Ltd.) were mixed with 97.5 parts by weight of isopropanol (Kanto Chemical Co., Inc.) and stirred to effect dissolution, following which 16.5 parts by weight of pyrrolidine was added under stirring. This mixture was heated and reacted for 7 hours under refluxing. The solids were separated off by vacuum filtration, following which the filtrate was vacuum concentrated, thereby giving a residue having a deep wine-red color. This residue was recrystallized, first from acetonitrile, then from an acetonitrile-tetrahydrofuran mixed solvent, giving 32 parts by weight of 1,1'-spirobipyrrolidinium bromide as a white solid.

Next, aside from using 1,1'-spirobipyrrolidinium bromide instead of N-2-methoxyethyl-N-methylpyrrolidinium chloride, Compound 2 was synthesized as a white solid by the same method as in Example 1. The ¹H-NMR spectrum of Compound 2 thus obtained is shown in FIG. 2.

Example 3

Synthesis of Compound 3

Compound 3 of the following formula was synthesized.

[Chemical Formula 15]

Compound 3

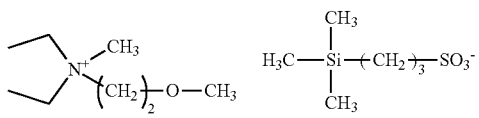

Diethylamine (Kanto Chemical Co., Inc.), 71 parts by weight, and 2-methoxyethyl chloride (Kanto Chemical Co., Inc.), 88 parts by weight, were mixed together and reacted at 120° C. for 24 hours in an autoclave. At this time, the maximum internal pressure reached was 4.5 kgf/cm² (0.44 MPa). After 24 hours, the crystals that deposited out were washed using tetrahydrofuran (Wako Pure Chemical Industries, Ltd.) and separated out by filtration. The filtrate was distilled at standard pressure, giving 81 parts by weight of a fraction boiling near 135° C. This compound was confirmed by NMR to be 2-methoxyethyldiethylamine.

Next, 9.0 parts by weight of 2-methoxyethyldiethylamine was dissolved in 80 parts by weight of tetrahydrofuran (Wako Pure Chemical Industries Co., Ltd.) and, while stirring the solution in an autoclave, 15% methyl chloride gas in nitrogen (Nittoku Kagaku Kogyo KK) was introduced therein. Methyl chloride gas was added until the internal pressure became 4 kgf/cm² (0.39 MPa), after which the temperature was gradually raised to 60° C. over 3 hours. The maximum internal pressure reached at this time was 5.4 kgf/cm² (0.53 MPa). The solution was then allowed to cool under continued stirring, and the crystals that settled out were separated off by filtration. The crystals were vacuum dried, giving 12 parts by weight of the target substance N,N-diethyl-N-methyl-N-2-methoxyethyl-ammonium chloride (DEMECl).

Next, aside from using N,N-diethyl-N-methyl-N-2-methoxyethylammonium chloride instead of N-2-methoxyethyl-N-methylpyrrolidinium chloride, Compound 3 was synthesized as a liquid by the same method as in Example 1. The ¹H-NMR spectrum of Compound 3 thus obtained is shown in FIG. 3.

Example 4

Synthesis of Compound 4

Compound 4 of the following formula was synthesized.

[Chemical Formula 16]

Compound 4

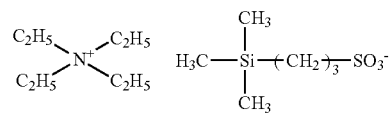

Aside from using tetraethylammonium chloride (Wako Pure Chemical Industries Co., Ltd.) instead of N-2-methoxyethyl-N-methylpyrrolidinium chloride, Compound 4 was synthesized as a white solid by the same method as in Example 1. The ¹H-NMR spectrum of Compound 4 thus obtained is shown in FIG. 4.

Example 5

Synthesis of Compound 5

Compound 5 of the following formula was synthesized.

[Chemical Formula 17]

Compound 5

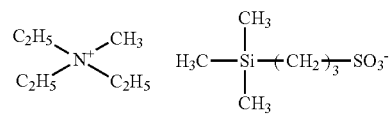

Aside from using triethylmethylammonium chloride (Tokyo Chemical Industry Co., Ltd.) instead of N-2-methoxyethyl-N-methylpyrrolidinium chloride, Compound 5 was synthesized as a white solid by the same method as in Example 1. The $^1$H-NMR spectrum of Compound 5 thus obtained is shown in FIG. 5.

Example 6

Synthesis of Compound 6

Compound 6 of the following formula was synthesized.

[Chemical Formula 18]

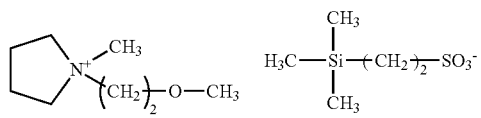

Compound 6

Aside from using sodium 2-(trimethylsilyl)-1-ethanesulfonate instead of sodium 3-(trimethylsilyl)-1-propanesulfonate, Compound 6 was synthesized as a liquid by the same method as in Example 1. The sodium 2-(trimethyl-silyl)-1-ethanesulfonate was synthesized in accordance with the method described in U.S. Pat. No. 3,141,898. The $^1$H-NMR spectrum of Compound 6 thus obtained is shown in FIG. 6.

Example 7

Synthesis of Compound 7

Compound 7 of the following formula was synthesized.

[Chemical Formula 19]

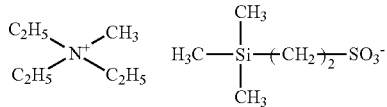

Compound 7

Aside from using triethylmethylammonium chloride (Tokyo Chemical Industry Co., Ltd.) instead of N-2-methoxyethyl-N-methylpyrrolidinium chloride, Compound 7 was synthesized as a white solid by the same method as in Example 6. The $^1$H-NMR spectrum of Compound 7 thus obtained is shown in FIG. 7.

Comparative Example 1

Synthesis of Compound 8

Compound 8 of the following formula was synthesized in accordance with the method described in JP-A 2007-161733.

[Chemical Formula 20]

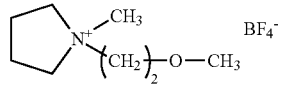

Compound 8

Example 8, Comparative Example 2

Cyclic Voltammetry Measurement 0.1 M Propylene carbonate (PC, Kishida Chemical Co., Ltd.) solutions were prepared of each of above Compounds 1 to 5 and also, as a comparative example, of both the tetraethylammonium tetrafluoroborate (TEABF$_4$, Kanto Chemical Co., Inc.) commonly used as the electrolyte salt in electrical double-layer capacitors that use an organic electrolyte and above Compound 8, and cyclic voltammetry measurements were carried out.

The results are shown in FIG. 8. As is apparent from the graph, Compounds 1 to 5 have wide potential windows and are electrochemically stable, thus indicating them to be useful as electrolyte salts for use in electrical double-layer capacitors.

Example 9, Comparative Example 3

Cyclic Voltammetry Measurement 0.1 M PC solutions were prepared of each of above Compounds 6 and 7 and also, as a comparative example, of both TEABF$_4$ and above Compound 8, and cyclic voltammetry measurements was carried out.

The results are shown in FIG. 9. As is apparent from the graph, Compounds 6 and 7 have wide potential windows and are electrochemically stable, thus indicating them to be useful as electrolyte salts for use in electrical double-layer capacitors.

The invention claimed is:

1. An electrolyte salt for electrical storage devices, comprising a quaternary ammonium cation of formula (1) below and a trimethylsilyl alkanesulfonate anion of formula (2) below

(1)

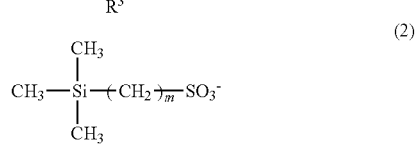

(2)

wherein R$^1$ to R$^4$ are each independently an alkyl group of 1 to 4 carbons or an alkoxyalkyl group of the formula —(CH$_2$)$_n$—OR, with the proviso that at least one of R$^1$ to R$^4$ is an alkoxyalkyl group of the formula —(CH$_2$)$_n$—OR; R is a methyl group or an ethyl group; n is 1 or 2; and m is 2 or 3.

2. The electrolyte salt for electrical storage devices of claim 1, wherein n is 2.

3. An electrolyte salt for electrical storage devices, comprising a quaternary ammonium cation of formula (1) below and a trimethylsilyl alkanesulfonate anion of formula (2 ) below

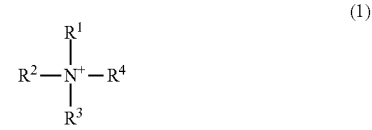

(1)

-continued

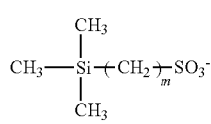

(2)

wherein $R^1$ to $R^4$ are each independently an alkyl group of 1 to 4 carbons or an alkoxyalkyl group of the formula —$(CH_2)_n$—OR, with the proviso that any two of $R^1$ to $R^4$ are bonded to each other and form a ring together with the nitrogen atom to which they are bonded and optionally the remaining two are bonded to each other and form a spiro ring with the nitrogen group serving as the spiro atom; R is a methyl group or an ethyl group; n is 1 or 2; and m is 2 or 3.

4. The electrolyte salt for electrical storage devices of claim 3, wherein the ring is a pyrrolidine ring or the spiro ring is a 1,1'-spirobipyrrolidine ring.

5. An electrolyte salt for electrical storage devices, comprising a quaternary ammonium cation selected from the group consisting of formulas (4) to (6) below and a trimethylsilyl alkanesulfonate anion of formula (2) below

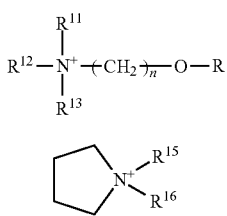

(4)

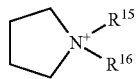

(5)

-continued

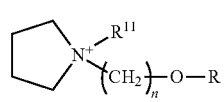

(6)

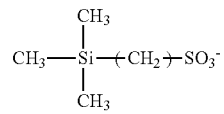

(2)

wherein $R^{11}$ to $R^{13}$ are each independently alkyl groups of 1 to 4 carbons; $R^{15}$ and $R^{16}$ are each independently alkyl groups of 1 to 4 carbons, with the proviso that $R^{15}$ and $R^{16}$ may be bonded to each other and may form a ring together with the nitrogen atom to which they are bonded; R is a methyl group or an ethyl group; n is 1 or 2; and m is 2 or 3.

6. An electrolyte containing the electrolyte salt for electrical storage devices of claim 1.

7. An electrical storage device containing the electrolyte of claim 6.

8. The electrical storage device of claim 7 which is an electrical double-layer capacitor.

9. The electrical storage device of claim 7 which is an electrolytic capacitor.

10. An electrolyte containing the electrolyte salt for electrical storage devices of claim 2.

11. An electrolyte containing the electrolyte salt for electrical storage devices of claim 3.

12. An electrolyte containing the electrolyte salt for electrical storage devices of claim 4.

13. An electrolyte containing the electrolyte salt for electrical storage devices of claim 5.

* * * * *